United States Patent [19]

Schmid

[11] 4,225,506

[45] Sep. 30, 1980

[54] PROCESS FOR MANUFACTURING A DIKETONE

[75] Inventor: Max Schmid, Brugg, Switzerland

[73] Assignee: Hoffmann-La Roche Inc., Nutley, N.J.

[21] Appl. No.: 38,760

[22] Filed: May 14, 1979

[30] Foreign Application Priority Data

May 30, 1978 [CH] Switzerland .................. 5883/78

[51] Int. Cl.$^3$ .......................................... C07D 307/60
[52] U.S. Cl. ................................................... 260/343.6
[58] Field of Search ...................................... 260/343.6

[56] References Cited

U.S. PATENT DOCUMENTS

| | | | |
|---|---|---|---|
| 3,996,246 | 12/1976 | Hoffmann et al. | 260/332.2 |
| 3,996,259 | 12/1976 | Lee et al. | 260/348.18 |
| 4,062,868 | 12/1977 | Confalone et al. | 260/332.2 |

FOREIGN PATENT DOCUMENTS

| | | |
|---|---|---|
| 1033652 | 7/1958 | Fed. Rep. of Germany . |
| 32628 | 10/1964 | German Democratic Rep. . |
| 41651 | 11/1967 | German Democratic Rep. . |
| 37505 | 1/1968 | German Democratic Rep. . |
| 1183387 | 3/1970 | United Kingdom . |

OTHER PUBLICATIONS

Richard Kuhn et al., Berichte, vol. 75 (1942), pp. 121-123.
S. H. Lipton et al., Jour. Am. Chem. Soc., vol. 71 (1949) pp. 2364-2367.
O. Nagase et al., Chem. Pharm. Bull., vol. 17 (1969) pp. 398-399.
G. A. Lee et al., Tetrahedron Letters, No. 20 (1976), pp. 1641-1644.

*Primary Examiner*—Norma S. Milestone
*Attorney, Agent, or Firm*—Jon S. Saxe; Bernard S. Leon; George W. Johnston

[57] ABSTRACT

A process for producing dihydro-4,4-dimethyl-2,3-furandione by oxidizing dihydro-3-hydroxy-4,4-dimethyl-2(3H)-furanone with a solid alkali metal hypochlorite or alkaline earth metal hypochlorite in an organic phase is disclosed.

10 Claims, No Drawings

PROCESS FOR MANUFACTURING A DIKETONE

BACKGROUND OF THE INVENTION

1. Field of the Invention

The present invention concerns a process for manufacturing a diketone, namely dihydro-4,4-dimethyl-2,3-furandione.

2. Description of the Prior Art

Dihydro-4,4-dimethyl-2,3-furandione is also known as ketopantolactone. This compound is an important starting material for producing optically active dihydro-3-hydroxy-4,4-dimethyl-2(3H)-furanone, also known as pantolactone.

In the prior art, dihydro-4,4-dimethyl-2,3-furandione was obtained by oxidizing dihydro-3-hydroxy-4,4-dimethyl-2(3H)-furanone with lead tetraacetate, N-bromosuccinimide and $CrO_3$ (Jones reagent) as the oxidizing agent. The prior art procedure disadvantageously resulted in relatively low yield of dihydro-4,4-dimethyl-2,3-furandione. Additionally, the oxidizing agent of the prior art procedure was expensive.

I have discovered a process for producing dihydro-3-hydroxy-4,4-dimethyl-2,3-furandione in relatively high yields and without utilizing the expensive oxidizing agents of the prior art.

SUMMARY OF THE INVENTION

This invention concerns a process for producing dihydro-4,4-dimethyl-2,3-furandione (ketopantalactone).

In accordance with the invention, the desired dihydro-4,4-dimethyl-2,3-furandione is manufactured in substantially higher yields and with cheaper oxidizing agents than hitherto by oxidizing dihydro-3-hydroxy-4,4-dimethyl-2(3H)-furanone with a solid alkali metal hypochlorite or alkaline earth metal hypochlorite in an organic phase.

DETAILED DESCRIPTION OF THE PRESENT INVENTION

This invention concerns a process for manufacturing dihydro-4,4-dimenthyl-2,3-furandione.

In the invention, dihydro-3-hydroxy-4,4-dimethyl-2(3H)-furanone is oxidized with a solid alkali metal hypochlorite or alkaline earth metal hypochlorite. The oxidation occurs in a solvent in which dihydro-3-hydroxy-4,4-dimethyl-2(3H)-furanone and dihydro-4,4-dimethyl-2,3-furandione are substantially soluble therein, but the alkali metal hypochlorite or alkaline earth hypochlorite is substantially insoluble therein.

The oxidation in accordance with the present invention thus is a heterogeneous oxidation in which the oxidizing agent is substantially insoluble in the liquid phase.

Preferred solid alkali metal hypochlorite or alkaline earth metal hypochlorite oxidizing agents include calcium hypochlorite, barium hypochlorite or lithium hypochlorite. Calcium hypochlorite is particularly preferred.

The term "calcium hypochlorite" also includes chloride of lime which consists to a substantial extend of calcium hypochlorite.

The specific hypochlorite employed as the oxidizing agent preferably is dried by any conventional technique, before it is utilized in the present process. It is, however, not necessary to remove the water of crystallization from the oxidizing agent (for example, in the case of calcium hypochlorite 3 mol of water of crystallization).

The hypochlorite employed as the oxidizing agent preferably is used in about equimolar amounts or in a slight excess.

Consistent with the nature of the present heterogeneous oxidation, there is utilized a solvent in which the starting material (dihydro-3-hydroxy-4,4-dimethyl-2(3H)-furanone) and the end product (dihydro-4,4-dimethyl-2,3-furandione) of the invention are soluble but in which the oxidizing agent is substantially insoluble. Suitable solvents include hydrocarbons or chlorinated hydrocarbons which are not sensitive to oxidation (e.g., benzene, methylene chloride, chloroform and hexane) as well as ether (e.g., diethylether), acetonitrile and the like. Preferred solvents are benzene, methylene chloride and acetonitrile.

The amount of solvent used in the process of the present invention preferably should be sufficient to bring all of the starting material into solution and to provide a mixture which can still be stirred.

The oxidation in accordance with the present invention is conveniently carried out at a temperature of about 0° to about 40° C., preferably at room temperature (about 20° to about 25° C.).

In general, the oxidation is completed in a few hours; for example, between about 4 hours and about 15 hours.

By filtering the mixture obtained after carrying out the oxidation, there is obtained a solution which, after evaporation, gives the desired dihydro-4,4-dimethyl-2,3-furandione in yields of about 70–90% by weight.

The following non-limiting examples further illustrate the invention. Unless otherwise stated, percentages are weight percentages and temperatures are in degrees Celsius.

EXAMPLE 1

107.5 g of a commercially available, previously dried calcium hypochlorite preparation, corresponding to 78 g of calcium hypochlorite, and 500 ml of acetonitrile dried over molecular sieves are placed in a 1 litre flask which is fitted with a mechanical stirrer, a reflux condenser, a dropping funnel and a thermometer.

To this mixture is added dropwise within 30 minutes with vigorous stirring a solution of 63.4 g. of racemic dihydro-3-hydroxy-4,4-dimethyl-2(3H)-furanone (DL-pantolactone) in 250 ml of dry acetonitrile.

Subsequently, the mixture is stirred at room temperature for 4 hours, filtered through a glass frit and the residue is washed with 150 ml of acetonitrile. After removing the solvent of a rotary evaporator and drying under reduced pressure, there are obtained 49 g of the desired dihydro-4,4-dimethyl-2,3-furandione of melting point 61°-64° C. After recrystallization from diethylether, there are obtained 45 g of pure diketone of melting point 66°-67° C.

The calcium hypochlorite preparation used in this Example was obtained by drying a commercially available product in a drying oven at 60°-70° C. and in a high vacuum for 24 hours. This commercially available preparation contained 65% calcium hypochlorite, 15% sodium chloride, 10% water and about 10% calcium carbonate, together with other impurities.

In place of the aforementioned calcium hypochlorite preparation there can also be used commercially available calcium hypochlorite containing 3 mol of water of crystallization or a preparation having a lower water of crystallization content.

As the oxidizing agent there can also be used dried and powdered chloride of lime having a calcium hypochlorite content of about 30%.

EXAMPLE 2

In a flask similar to that described in Example 1 there is added dropwise to a mixture of 136.9 g of calcium hypochlorite [Ca(OCl)$_2$.2H$_2$O (65%)] and 500 ml of methylene chloride with vigorous stirring within 40 minutes a solution of 65 g of DL-pantolactone in 250 ml of methylene chloride, the internal temperature rising to about 35° C. The mixture is stirred overnight at room temperature and subsequently filtered through a glass frit. The residue is washed with 200 ml of fresh methylene chloride. After removing the solvent in a rotary evaporator and drying, the yield of ketopantolactone amounts to 48 g (75%). This can be purified by recrystallization from ether in accordance with Example 1.

EXAMPLE 3

80 g of dried lithium hypochlorite (ca 35% active chlorine, 30% LiOCl) and 300 ml of dry benzene are placed in a 500 ml flask which is fitted with a mechanical stirrer, a reflux condenser, a droping funnel and a thermometer. To this mixture is added dropwise within 30 minutes with vigorous stirring a solution of 26 g of racemic dihydro-3-hydroxy-4,4-dimethyl-2(3H)-furanone (DL-pantolactone) in 100 ml of dry benzene. The mixture is stirred overnight and then contained 52% (according to gas chromatography) of the desired dihydro-4,4-dimethyl-2,3-furandione.

I claim:

1. A process for manufacturing dihydro-4,4-dimethyl-2,3-furandione, which process comprises oxidizing dihydro-3-hydroxy-4,4-dimethyl-2(3H)-furanone with a solid alkali metal hypochlorite or a solid alkaline earth metal hypochlorite, said oxidation occurring in a solvent in which dihydro-3-hydroxy-4,4-dimethyl-2(3H)-furanone and dihydro-4,4-dimethyl-2,3-furandione are substantially soluble therein but in which said alkalimetal hypochlorite or alkaline earth metal hypochlorite is substantially insoluble therein.

2. The process of claim 1 wherein dihydro-3-hydroxy-4,4-dimethyl-2(3H)-furanone is oxidized with said solid alkali metal hypochlorite.

3. The process of claim 2 wherein the alkali metal hypochlorite is lithium hypochlorite.

4. The process of claim 1 wherein dihydro-3-hydroxy-4,4-dimethyl-2(3H)-furanone is oxidized with said solid alkaline earth metal hypochlorite.

5. The process of claim 4 wherein the alkaline earth metal hypochlorite is calcium hypochlorite or barium hypochlorite.

6. The process of claim 1 wherein the solvent is benzene, methylene chloride, chloroform or acetonitrile.

7. The process of claim 1 wherein the oxidation is carried out at a temperature of about 10° to about 40° C.

8. The process of claim 7 wherein the oxidation is carried out at about 20° to about 25° C.

9. A process for producing dihydro-4,4-dimethyl-2,3-furandione, comprising oxidizing dihydro-3-hydroxy-4,4-dimethyl-2(3H)-furanone with an oxidizing agent selected from the group consisting of calcium hypochlorite, barium hypochlorite and lithium hypochlorite in a solvent selected from the group consisting of benzene, methylene chloride, chloroform and acetonitrile.

10. A process for the manufacture of dihydro-4,4-dimethyl-2,3-furandione, which process comprises oxidizing dihydro-3-hydroxy-4,4-dimethyl-2(3H)-furanone with a solid alkali metal hypochlorite or alkaline earth metal hypochlorite in an organic phase.

* * * * *